US012746004B2

(12) United States Patent
Shelton, IV et al.

(10) Patent No.: US 12,746,004 B2

(45) Date of Patent: Sep. 29, 2026

(54) IMPLANTABLE SPHINCTER ASSISTANCE DEVICE WITH DEFORMABLE ELEMENTS

(71) Applicant: Cilag GmbH International, Zug (CH)

(72) Inventors: Frederick E. Shelton, IV, Hillsboro, OH (US); Kevin M. Fiebig, Cincinnati, OH (US); Joshua D. Young, West Orange, NJ (US)

(73) Assignee: Cilag GmbH International, Zug (CH)

( * ) Notice: Subject to any disclaimer, the term of this patent is extended or adjusted under 35 U.S.C. 154(b) by 1251 days.

(21) Appl. No.: 17/682,153

(22) Filed: Feb. 28, 2022

(65) Prior Publication Data

US 2022/0257257 A1 Aug. 18, 2022

Related U.S. Application Data

(62) Division of application No. 16/225,643, filed on Dec. 19, 2018, now Pat. No. 11,298,136.

(51) Int. Cl.

*A61B 17/12* (2006.01)
*A61B 17/02* (2006.01)
(Continued)

(52) U.S. Cl.

CPC .... *A61B 17/12099* (2013.01); *A61B 17/0293* (2013.01); *A61B 17/12009* (2013.01);
(Continued)

(58) Field of Classification Search

CPC .......... A61B 17/0293; A61B 17/12009; A61B 17/12013; A61B 2017/00827;
(Continued)

(56) References Cited

U.S. PATENT DOCUMENTS 5,122,136 A 6/1992 Guglielmi et al.
5,204,382 A 4/1993 Wallace et al.
(Continued)

FOREIGN PATENT DOCUMENTS

DE 3011742 A1 10/1981
EP 1547549 A2 6/2005
(Continued)

*Primary Examiner* — Christine H Matthews
(74) *Attorney, Agent, or Firm* — FBT Gibbons LLP

(57) ABSTRACT

A sphincter augmentation device includes a plurality of interlinked bodies and a pair of device ends configured to releasably couple together to secure the bodies in a loop formation sized to fit around an internal anatomical passageway of a patient. The device further includes a plurality of resilient members, with each resilient member extending between an adjacent pair of the bodies. The resilient members are configured to elastically deform to permit the device to transition between a radially contracted state and a radially expanded state. The resilient members bias the device toward the radially contracted state in which the device exerts an inwardly directed force on the anatomical passageway to selectively limit passage of fluids therethrough. The device further includes an expansion limiting member that extends between and is slidably received by an adjacent pair of the bodies, and is configured to limit radial expansion of the device.

18 Claims, 14 Drawing Sheets

(51) Int. Cl.
*A61B 90/00* (2016.01)
*A61F 2/04* (2013.01)
*A61B 17/00* (2006.01)

(52) U.S. Cl.
CPC ................ *A61B 90/02* (2016.02); *A61F 2/04* (2013.01); *A61B 2017/00827* (2013.01); *A61B 2017/00876* (2013.01); *A61B 2017/12018* (2013.01); *A61F 2002/044* (2013.01); *A61F 2250/0007* (2013.01)

(58) Field of Classification Search
CPC ........... A61B 2017/00862; A61B 2017/00876; A61B 90/02; A61F 2/04
See application file for complete search history.

(56) References Cited

U.S. PATENT DOCUMENTS

| | | | |
|---|---|---|---|
| 5,509,888 | A | 4/1996 | Miller |
| 5,702,361 | A | 12/1997 | Evans, II et al. |
| 6,543,456 | B1 | 4/2003 | Freeman |
| 7,175,589 | B2 | 2/2007 | Deem et al. |
| 7,374,565 | B2 | 5/2008 | Hassler, Jr. et al. |
| 7,390,294 | B2 | 6/2008 | Hassler. , Jr. |
| 7,445,010 | B2 | 11/2008 | Kugler et al. |
| 7,481,763 | B2 | 1/2009 | Hassler, Jr. et al. |
| 7,695,427 | B2 | 4/2010 | Kugler et al. |
| 7,727,141 | B2 | 6/2010 | Hassler, Jr. et al. |
| 7,879,068 | B2 | 2/2011 | Dlugos et al. |
| 8,070,670 | B2 | 12/2011 | Deem et al. |
| 8,603,023 | B2 | 12/2013 | Albrecht et al. |
| 8,617,049 | B2 | 12/2013 | Dlugos, Jr. et al. |
| 8,636,751 | B2 | 1/2014 | Albrecht et al. |
| 8,715,157 | B2 | 5/2014 | Berg et al. |
| 8,734,475 | B2 | 5/2014 | Ekvall et al. |
| 8,870,742 | B2 | 10/2014 | Dlugos, Jr. et al. |
| 8,876,761 | B2 | 11/2014 | Albrecht et al. |
| 10,405,865 | B2 | 9/2019 | Shelton, IV et al. |
| 10,813,737 | B2 | 10/2020 | Auld et al. |
| 10,828,064 | B2 | 11/2020 | Flakne et al. |
| 10,945,738 | B2 | 3/2021 | Auld et al. |
| 11,298,136 | B2 | 4/2022 | Shelton, IV et al. |
| 2005/0283235 | A1 | 12/2005 | Kugler et al. |
| 2009/0062824 | A1 | 3/2009 | Berg et al. |
| 2011/0098731 | A1 | 4/2011 | Whitbrook et al. |
| 2013/0053874 | A1 * | 2/2013 | Ekvall .............. A61B 17/12013 606/157 |
| 2014/0336696 | A1 | 11/2014 | Kugler et al. |
| 2017/0055986 | A1 | 3/2017 | Harris et al. |
| 2018/0325643 | A1 * | 11/2018 | Kappus ................. A61F 2/0004 |
| 2019/0029689 | A1 | 1/2019 | Shelton, IV et al. |
| 2019/0274803 | A1 | 9/2019 | Auld et al. |

FOREIGN PATENT DOCUMENTS

| | | | |
|---|---|---|---|
| WO | WO 1993/015721 | A1 | 8/1993 |
| WO | WO 1993/016658 | A1 | 9/1993 |
| WO | WO 1993/019702 | A1 | 10/1993 |
| WO | WO 1997/033632 | A2 | 9/1997 |
| WO | WO 1998/044965 | A1 | 10/1998 |
| WO | WO 2000/054835 | A1 | 9/2000 |
| WO | WO 2001/047431 | A2 | 4/2001 |

* cited by examiner

IMPLANTABLE SPHINCTER ASSISTANCE DEVICE WITH DEFORMABLE ELEMENTS

This application is a divisional of U.S. patent application Ser. No. 16/225,643, filed Dec. 19, 2018, and issued as U.S. Pat. No. 11,298,136 on Apr. 12, 2022.

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, healthy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
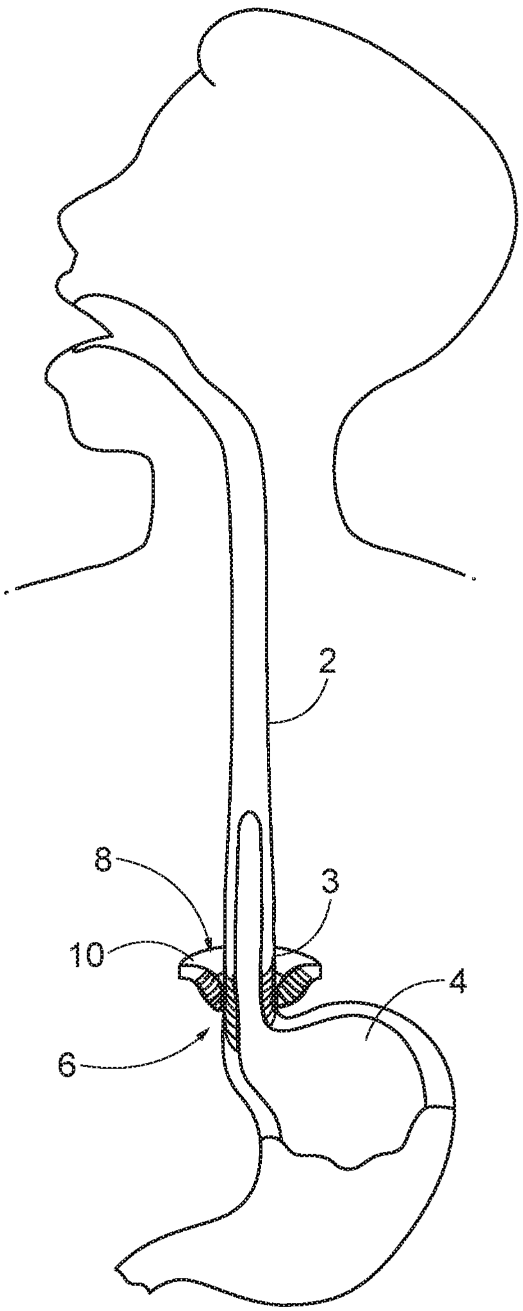
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Sphincter Augmentation Device

Figure 2:
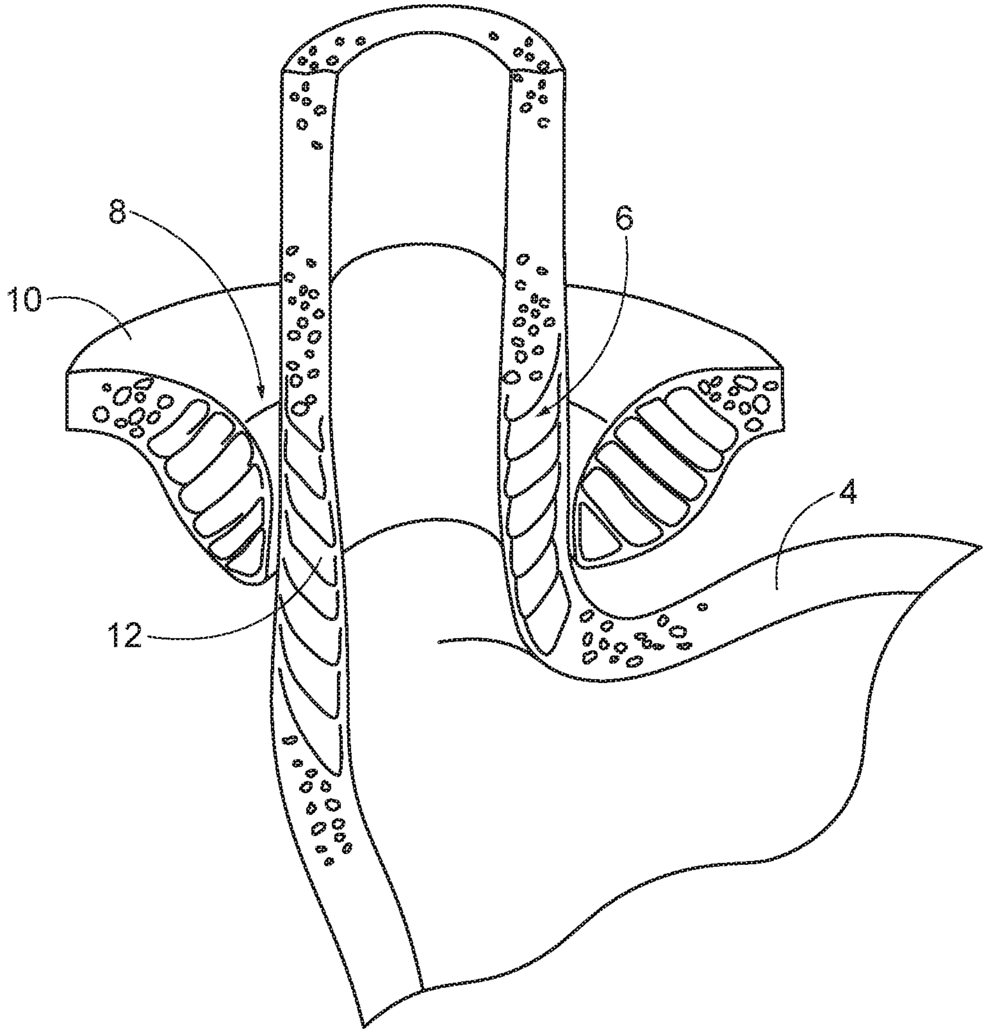
FIG. 2 depicts a cross-sectional isometric view, taken along a coronal plane of the body, of a human esophago-gastric junction.
Figure 3:
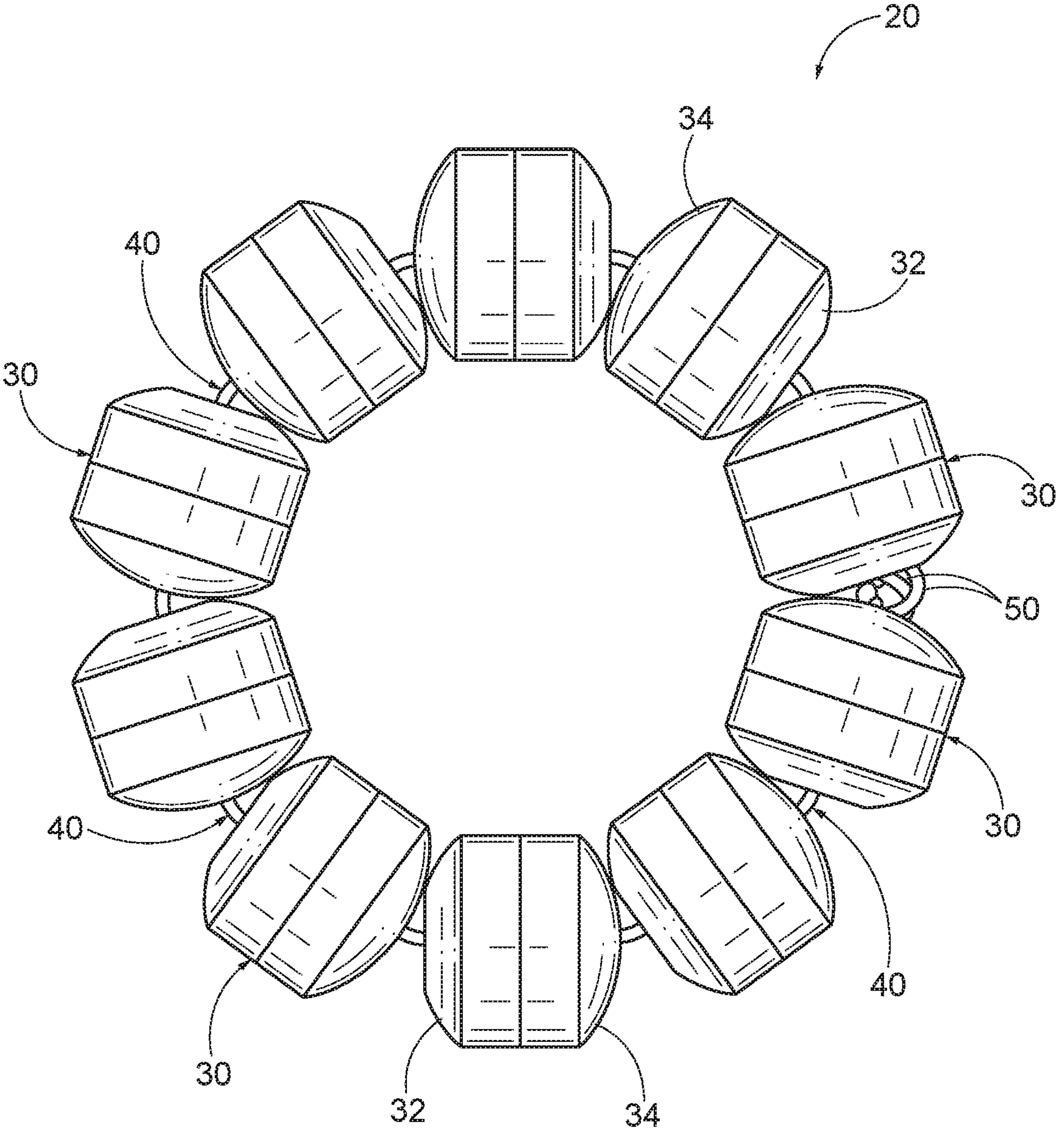
FIG. 3 depicts a top plan view of an exemplary sphincter augmentation device.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state to act as a valve. In other words, a healthy LES (6) may transition from the occluded state to the opened state to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Figure 4:
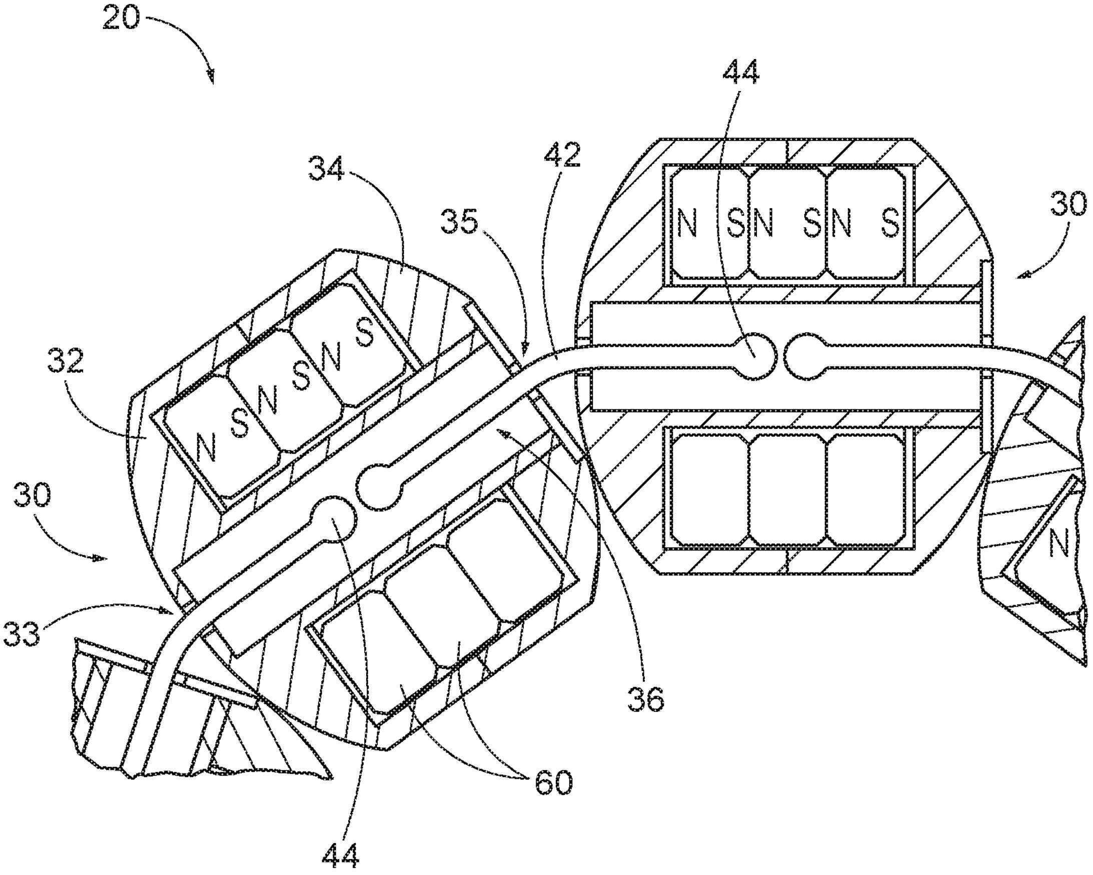
FIG. 4 depicts a cross-sectional view of a portion of the sphincter augmentation device of FIG. 3.

FIGS. 3-5B show an exemplary sphincter augmentation device (20) that may be used as an implant around a malfunctioning LES (6) to assist the LES (6) in transitioning between the occluded state and the opened state. Device (20) of this example comprises a plurality of beads (30) that are joined together by a plurality of links (40). Each bead (30) comprises a pair of housings (32, 34) that are securely fastened to each other. By way of example only, housings (32, 34) may be formed of a non-ferrous material (e.g., titanium, plastic, etc.). Each bead (30) further comprises a plurality of annular or toroidal rare-earth permanent magnets (60) that are stacked next to each other within housings (32, 34). In the present example, magnets (60) are completely sealed within beads (30). As best seen in FIG. 4, each bead (30) also defines a chamber (36) that is configured to slidably receive a portion of a respective pair of links (40). Housing (32) defines an opening (33) at one end of chamber (36); while housing (34) defines an opening (35) at the other end of chamber (36).

Each link (40) of the present example comprises a wire (42) that is pre-bent to form an obtuse angle. The free end of each wire (42) terminates in a ball tip (44). Beads (30) are joined together by links (40) such that a first end portion of a link (40) is in one bead (30), a second end portion of the same link (40) is in an adjacent bead (30), and an intermediate portion of the same link (40) is positioned between those two beads (30). Chambers (36) of beads (30) are configured to freely receive ball tips (44) and adjacent regions of wires (42); while openings (33, 35) are configured to prevent ball tips (44) from exiting chambers (36). Openings (33, 35) are nevertheless sized to allow wire (42) to slide through openings (33, 35). Thus, links (40) and beads (30) are configured to allow beads (30) to slide along links (40) through a restricted range of motion.

Figure 5A:
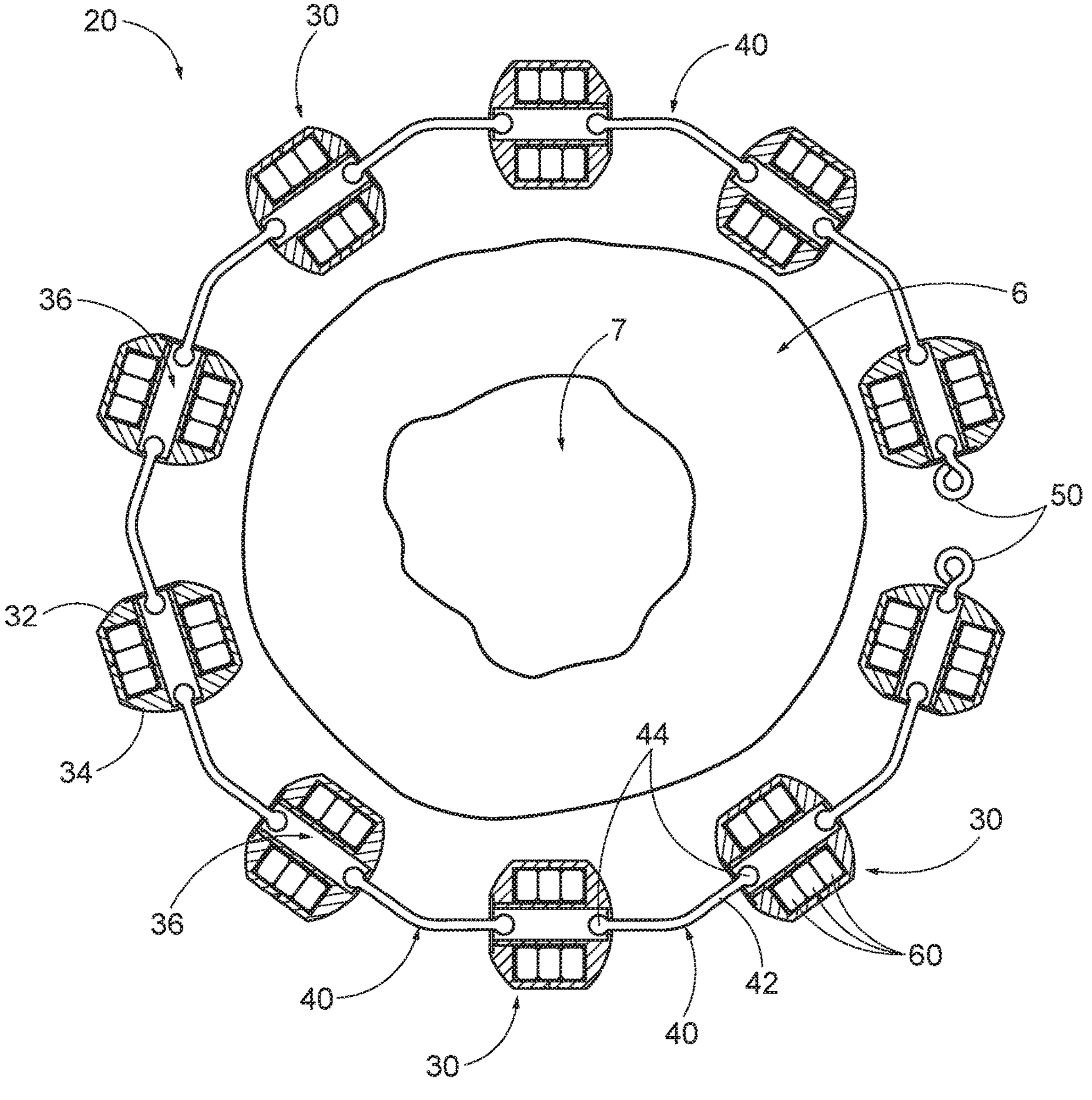
FIG. 5A depicts a cross-sectional top view of the sphincter augmentation device of FIG. 3 positioned about an LES, showing the sphincter augmentation device in an open and expanded state.
Figure 5B:
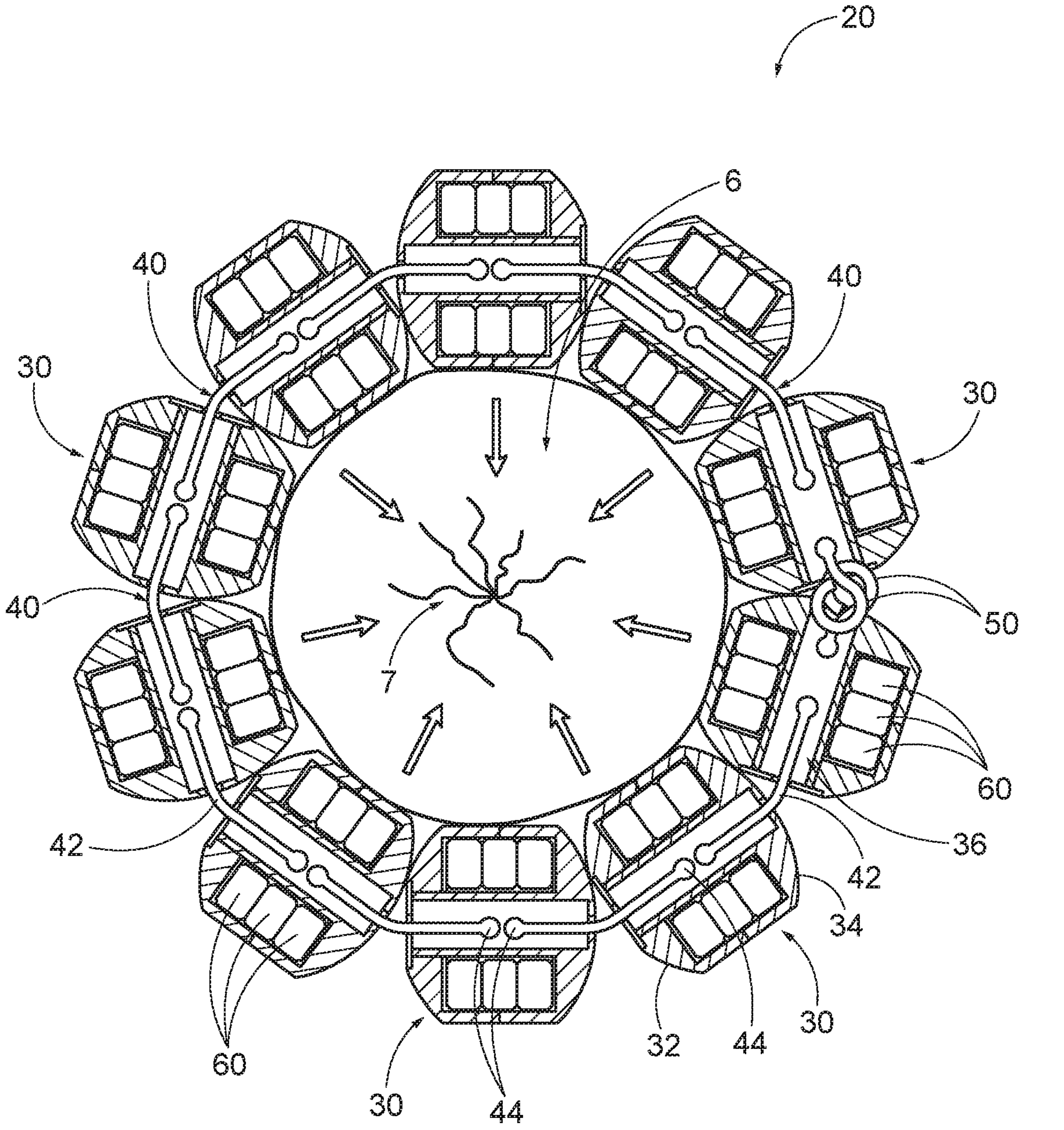
FIG. 5B depicts a cross-sectional top view of the sphincter augmentation device of FIG. 3 positioned about the LES of FIG. 5A, showing the sphincter augmentation device in a closed and contracted state.

As best seen in FIGS. 5A-5B, two beads (30) have opposing fastener features (50) that allow the ends of device (20) to be coupled together to form a loop. In the present example, fastener features (50) comprise eyelets. In some other versions, fastener features (50) comprise complementary clasp features, such as those disclosed in U.S. patent application Ser. No. 15/914,381, entitled "Tunable Magnetic Sphincter Augmentation Device," filed Mar. 7, 2018, issued as U.S. Pat. No. 10,945,738 on Mar. 16, 2021, the disclosure of which is incorporated by reference herein. As another merely illustrative example, fastener features (50) may be configured and operable in accordance with one or more of the teachings of U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein. Other suitable ways in which the ends of device (20) may be coupled together to form a loop will be apparent to those of ordinary skill in the art in view of the teachings herein. Those of ordinary skill in the art will also recognize that it may be desirable to provide fastener features (50) that can be decoupled if it becomes necessary or otherwise warranted to remove device (20) from the patient.

FIG. 5A shows device (20) in an open, expanded state, with device (20) being positioned about LES (6). At this stage, the opening (7) defined by LES (6) is in a persistently open state (e.g., allowing the patient to undesirably experience GERD and/or other undesirable conditions), warranting the securement of device (20) about the LES (6). FIG. 5B shows device (20) secured about the LES (6), with device (20) in a closed, contracted state. Device (20) is secured closed via fastener features (50). Magnets (60) are oriented within beads (30) such that each bead (30) will be magnetically attracted to the adjacent bead (30) in device (20). In other words, beads (30) are magnetically attracted to each other to magnetically bias device (20) toward the contracted configuration shown in FIG. 5B.

With device (20) secured around the LES (6) and in the contracted configuration, device (20) deforms the LES (6) radially inwardly to substantially close the opening (7) defined by the LES (6). In doing so, device (20) prevents the patient from experiencing GERD and/or other undesirable conditions that may be associated with a persistently open opening (7) at the LES (6). While magnets (60) have a tesla value that is high enough to substantially maintain opening (7) in a closed state to the point of preventing GERD and/or other undesirable conditions that may be associated with a persistently open opening (7), the tesla value of magnets (60) is low enough to allow LES (6) to expand radially outwardly to accommodate passage of a bolus of food, vomit, etc. through the opening (7) of LES (6). To accommodate such expansion, beads (30) may simply slide along links (40) to enlarge the effective diameter of device (20) as the bolus passes. After the bolus passes, the magnetic bias of magnets (60) will return device (20) to the contracted state shown in FIG. 5B. Device (20) thus ultimately prevents GERD and/or other undesirable conditions that may be associated with a persistently open opening (7); while still permitting the normal passage of food, etc. from the esophagus (2) to the stomach (4).

In addition to the foregoing, device (20) may be further configured and operable in accordance with any one or more of the teachings of U.S. Pat. No. 7,695,427, incorporated by reference above; U.S. patent application Ser. No. 15/664,665, issued as U.S. Pat. No. 10,405,865, incorporated by reference above; and/or U.S. patent application Ser. No. 15/914,381, issued as U.S. Pat. No. 10,945,738, incorporated by reference above.

II. Exemplary Sphincter Augmentation Devices Having Elastically Deformable Elements As described above, sphincter augmentation device (20) is biased toward a radially contracted state via magnetic attraction between permanent magnets (60) housed within beads (30). In some instances, it may be desirable to supplement or substitute such magnetic bias with resilient bias provided by resilient members that are resiliently (or "elastically") deformable. The following description addresses exemplary alternative sphincter augmentation devices (100, 200, 300, 400, 500 600) having such resilient members that enable devices (100, 200, 300, 400, 500 600) to transition between a radially contracted state and a radially expanded state, and which bias the devices toward the radially contracted state. Similar to device (20), each device (100, 200, 300, 400, 500 600) described below is configured to vary in its effective length (i.e., circumference) as it transitions between the contracted and expanded states. It will be understood that each device (100, 200, 300, 400, 500 600) is suitable to be implanted within a patient to facilitate proper functioning of an anatomical passageway. For instance, devices (100, 200, 300, 400, 500 600) may be positioned around a malfunctioning LES (6) to assist the LES (6) in transitioning between the occluded state and the opened state, similar to device (20) described above.

Figure 6A:
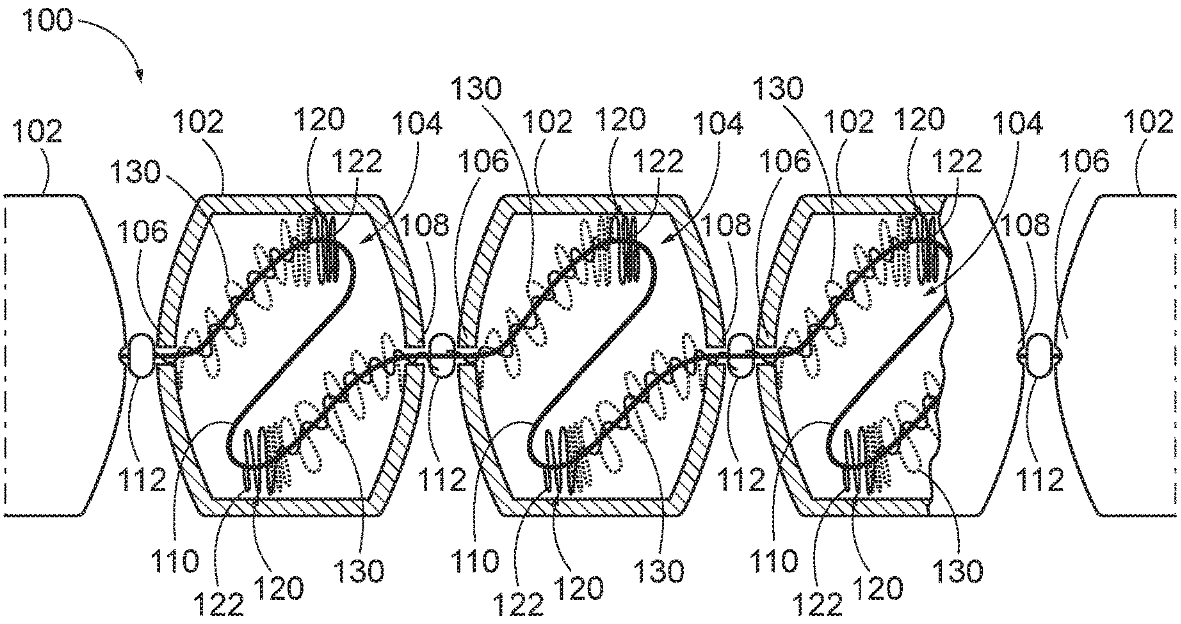
FIG. 6A depicts a partial cross-sectional top view of a portion of another exemplary sphincter augmentation device having extension springs and extension springs, showing the device in a contracted state.
Figure 6B:
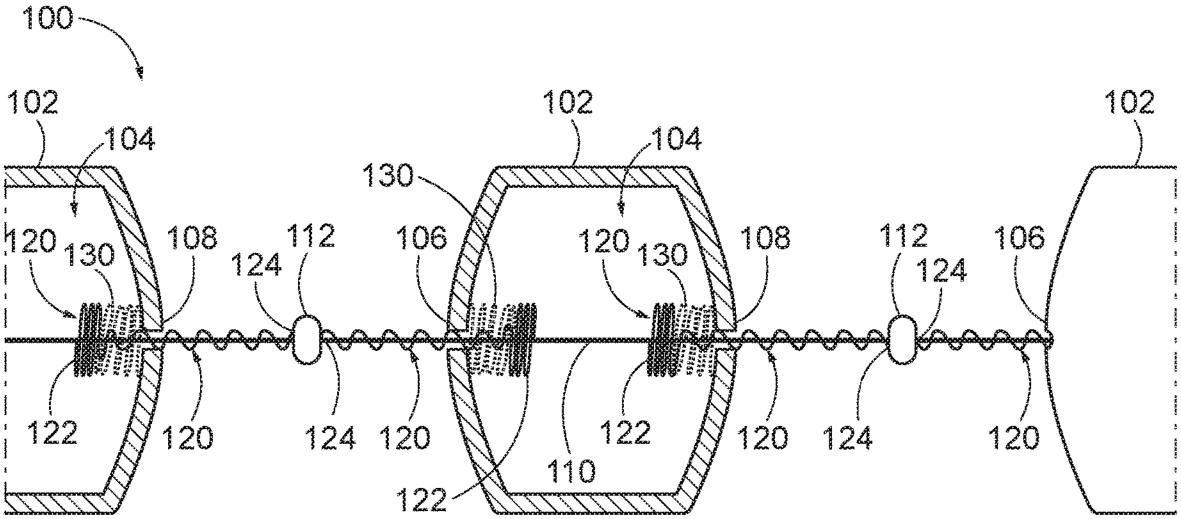
FIG. 6B depicts a partial cross-sectional top view of a portion of the sphincter augmentation device of FIG. 6A, showing the device in an expanded state.

A. Sphincter Augmentation Device Having Extension Springs and Compression Springs FIGS. 6A-6B show a portion of an exemplary sphincter augmentation device (100) having a plurality of bodies (102) that are interlinked by an elongate member in the form of a cable (110). Similar to device (20), device (100) includes a pair of opposed ends (not shown) configured to releasably couple together to secure bodies (102) in a loop formation around an anatomical passageway of a patient, such as esophagus (2). For instance, the opposed ends of device (100) may include coupling features similar to fastener features (50) described above or any of the exemplary coupling features of the references incorporated by reference herein.

Each body (102) of device (100) is formed with a generally bead-like shape having a hollow interior (104) and a pair of side openings (106, 108) formed in opposed sides of body (102) that confront adjacent bodies (102). Bodies (102) may be formed of a biocompatible metal, such as titanium, or of a polymeric material that exhibits greater resiliency than titanium. Cable (110) extends continuously through bodies (102) via side openings (106, 108) and interiors (104) along a length (or circumference) of device (100). A first end of cable (110) is anchored to a first end of device (100), and a second end of cable (110) is anchored to a second end of device (100). Bodies (102) are slidably disposed along cable (110) between the first and second device ends.

A plurality of spacer beads (112) are spaced longitudinally along cable (110) between the first and second device ends such that one spacer bead (112) is located between each adjacent pair of bodies (102). Spacer beads (112) of the present version are fixed to cable (110), though one or more of spacer beads (112) may be freely slidable along cable (110) in other versions. Spacer beads (112) provide a predetermined minimum spacing between each adjacent pair of bodies (102) when device is in a radially contracted state, shown in FIG. 6A. It will be appreciated that spacer beads (112) may be formed with any suitable thickness in a circumferential direction of device (100), and in any suitable quantity, to provide device (100) with a desired minimum circumference when the device ends are secured together to place device (100) in a closed, loop formation. As described below, bodies (102) are configured to slide along cable (110) between adjacent pairs of spacer beads (112) as device (100) expands and contracts.

Device (100) further includes a plurality of resilient members in the form of extension springs (120) and compression springs (130) that cooperate to bias device (100) toward a radially contracted state, shown in FIG. 6A, in which device (100) exhibits a reduced circumference.

Springs (120, 130) are configured to elastically deform to permit expansion of device (100) toward a radially expanded state, shown in FIG. 6B, in which device (100) exhibits an enlarged circumference. In the present example, each body (102) houses a pair of extension springs (120) that are disposed over cable (110). Each extension spring (120) has an inner spring end (122) oriented toward a center of body interior (104), and an outer spring end (124) that extends through one of opposed side openings (106, 108) such that the extension springs (120) of each body (102) extend in opposing directions along cable (110). Each inner spring end (122) is slidable over cable (110) and is formed with an enlarged diameter that prevents passage of inner spring end (122) through the respective side opening (106, 108) of body (102). Each outer spring end (124) is anchored to a respective spacer bead (112), externally of the respective body (102), and thus is fixed relative to cable (110) in the present version. In some versions, each extension spring (120) may extend continuously between an adjacent pair of bodies (102), such that a first end of spring (120) is retained within a first body (102) and an opposed second end of spring (120) is retained within an adjacent second body (102). In such versions, a medial portion of each extension spring (120) may be anchored to a respective spacer bead (112).

Each body (102) of the present example additionally houses a pair of compression springs (130) within body interior (104). As described below, compression springs (130) cooperate with extension springs (120) to resiliently bias device (100) toward the radially contracted state shown in FIG. 6A. Each compression spring (130) is positioned coaxially about a portion of a respective extension spring (120) such that an inner end of the compression spring (130) abuts and is anchored to the inner spring end (122) of the extension spring (120); and such that an opposed outer end of the compression spring (130) abuts and is anchored to an inner wall of body (102), through which a corresponding side opening (106, 108) extends.

Compression springs (130) may be configured with a spring rate (or "spring constant") that is different than a spring rate of extension springs (120), such that compression springs (130) begin to compress before or after extension springs (120) begin to extend when an expansion force is applied to device (100). Such versions of device (100) thus have a progressive (or "variable") spring rate. For instance, in some such versions, compression springs (130) may be configured with a greater spring rate than extension springs (120), such that extension springs (120) begin to extend before compression springs (130) begin to compress when an expansion force is applied to device (100). In other such versions, extension springs (120) may be configured with a greater spring rate than compression springs (130), such that compression springs (130) begin to compress before extension springs (120) begin to extend when an expansion force is applied to device (100).

As shown by the progression of FIG. 6A to FIG. 6B, when a radially outwardly directed expansion force is applied to the inner diameter of device (100) (e.g., by a food bolus passing through the encircled portion of distal esophagus (2)), bodies (102) slidably separate from one another circumferentially along cable (110). In doing so, each body (102) compresses its respective compression springs (130) inwardly against inner spring ends (122) of the respective extension springs (120). Inner spring ends (122) of extension springs (120) are thus driven inwardly toward the opposing inner wall of the respective body (102), such that each extension spring (120) exerts a circumferentially directed force on the spacer bead (112) to which it is anchored. The opposing forces exerted on each spacer bead (112), which itself is anchored to cable (110), cause each pair of extension springs (120) anchored to the spacer bead (112) to slidably extend along cable (110), such that outer spring ends (124) extend away from spacer bead (112), as shown in FIG. 6B. As described above, extension springs (120) and compression springs (130) may be provided with different spring rates, such that compression springs (130) begin to compress before or after extension springs (120) begin to extend.

As shown in FIGS. 6A-6B, portions of cable (110) may be coiled within body interiors (104) when device (100) is in the radially contracted state. Such portions of cable (110) are slidably withdrawn from body interiors (104) as device (100) expands. A maximum assumable length of cable (110) defines a maximum circumference that device (100) may assume while expanding. In this manner, cable (110) functions as an expansion limiting member. In the present version, cable (110) has a fixed length and is not configured to stretch or otherwise resiliently deform in response to an expansion force, such that expansion of device (100) halts when cable (110) reaches its fully extended state shown in FIG. 6B. In other versions, cable (110) may be configured to resiliently deform in some compacity by a predetermined amount, for example by stretching along its length, as device (100) transitions from the radially contracted state to the radially expanded state.

When a radial expansion force applied to expanded device (100) is removed, device (100) automatically returns to the radially contracted state shown in FIG. 6A via resiliency of extension springs (120) and compression springs (130). In particular, extension springs (120) slidably contract along cable (110), thereby drawing each adjacent pair of bodies (102) toward one another via their anchoring to spacer beads (112) positioned between bodies (102). Simultaneously, compression springs (130) extend within body interiors (104) to thereby retract extension springs (120) and the corresponding portions of cable (110) into body interiors (104), thereby drawing bodies (102) closer together. Retraction of the slack portions of extension springs (120) and cable (110) into body interiors (104) also ensures that such slack portions do not interfere with adjacent anatomical structures.

Optionally, though not shown, each body (102) of device (100) may additionally house one or more permanent magnets configured to magnetically attract the one or more magnets of adjacent bodies (102) in a manner similar to permanent magnets (60) of device (20) described above. Such magnets may cooperate with extension springs (120) and compression springs (130) to bias device (100) toward the radially contracted state of FIG. 6A. As described in greater detail below in connection with FIG. 7, the inclusion of such magnets may increase an initial expansion force required to radially expand device (100) from the fully contracted state of FIG. 6A.

Figure 7:
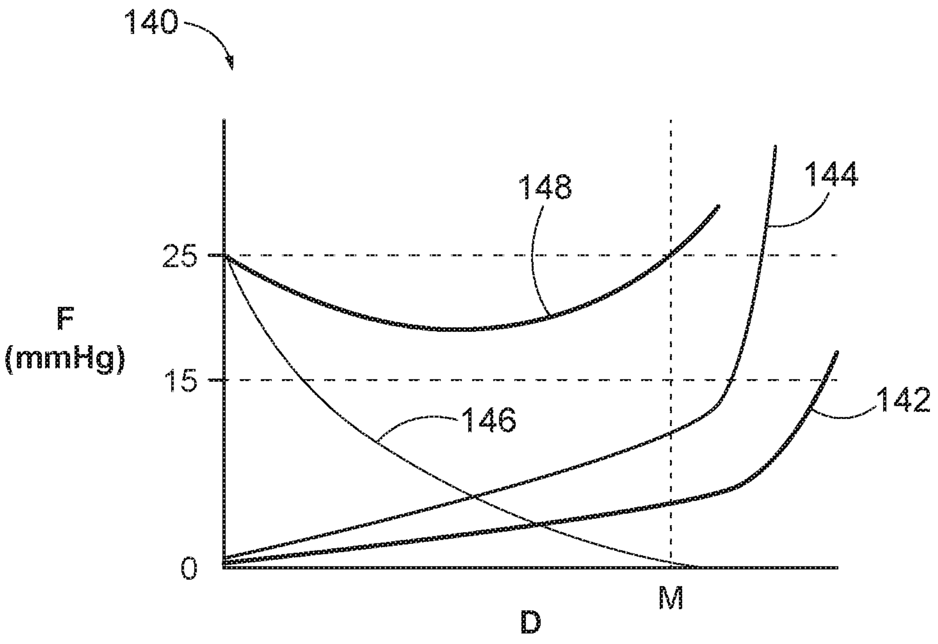
FIG. 7 depicts a line graph illustrating exemplary relationships between displacement and resulting contraction force exhibited by biasing members of a first exemplary version of the sphincter augmentation device of FIG. 6A.

FIG. 7 depicts an exemplary line graph (140) for a version of sphincter augmentation device (100) that incorporates permanent magnets similar to magnets (60), where extension springs (120) and compression springs (130) are not pre-loaded when device (100) is in the fully contracted state of FIG. 6A. The x-axis of graph (140) indicates circumferential separation (or displacement) (e.g., in millimeters or inches) of a given body (102) relative to an adjacent body (102), starting from the fully contracted state of device (100). The y-axis of graph (140) indicates resulting contraction forces exerted by springs (120, 130) and the magnets in millimeters of mercury (mmHg), in response to such circumferential displacement. As described above, cable (110) limits circumferential and thus radial expansion of device (100). Maximum circumferential displacement between adjacent bodies (102), as defined by cable (110), is indicated on graph (140) by vertical dashed line (M). Accordingly, the portion of graph (140) extending between zero circumferential displacement and maximum circumferential displacement (M) corresponds to an operational range of device (100).

Curve (142) of graph (140) represents a contraction force exerted by extension springs (120) in response to circumferential displacement of bodies (102). Curve (144) represents a contraction force exerted by compression springs (130) in response to circumferential displacement of bodies (102). Curve (146) represents a contraction force exerted by the magnets housed within bodies (102) in response to circumferential displacement of bodies (102). Curve (148) represents a cumulative contraction force exerted by springs (120, 130) and the magnets, collectively, in response to circumferential displacement of the bodies (102).

As shown by spring force curves (142, 144) of graph (140), extension springs (120) and compression springs (130) exert progressively increasing contraction forces as circumferential separation of bodies (102) increases during expansion of device (100). In contrast, as shown by magnetic force curve (146), the magnets exert a progressively decreasing contraction force as circumferential separation of bodies (102) increases. The resulting cumulative force shown by curve (148) thus decreases from an initial value, due to reduction of magnetic attraction forces; and then subsequently increases, due to an increase of resilient contraction forces exerted by springs (120, 130). In the illustrated example, device (100) of the above-described configuration (i.e., including magnets) exhibits maximum contraction forces at zero circumferential displacement and at maximum circumferential displacement (M), with a minimum contraction force being exhibited at approximately half-expansion of device (100).

Figure 8:
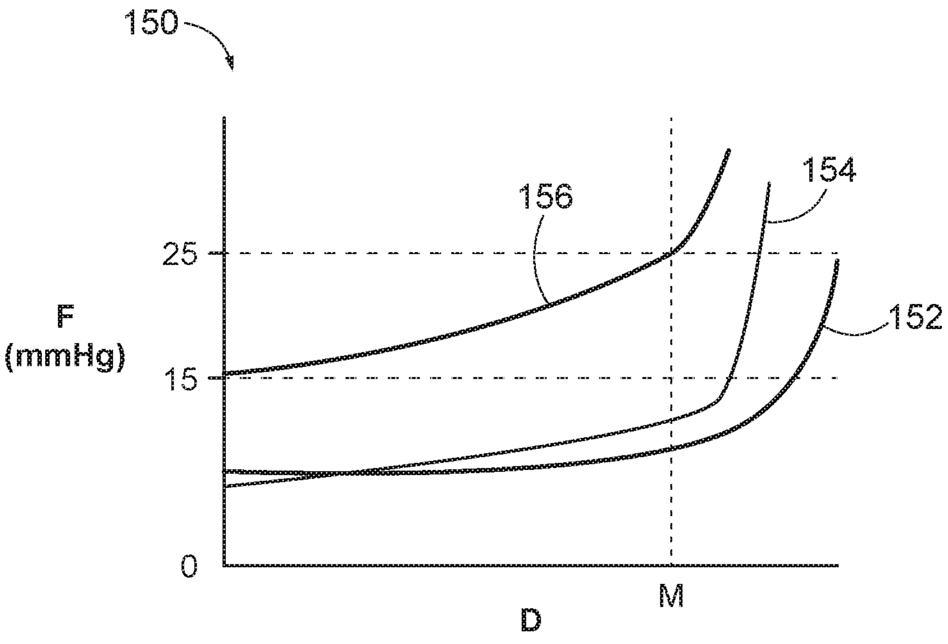
FIG. 8 depicts a line graph illustrating exemplary relationships between displacement and resulting contraction force exhibited by biasing members of a second exemplary version of the sphincter augmentation device of FIG. 6A.

In some instances, it may be desirable to omit magnets from bodies (102) of device (100). In such versions of device (100), extension springs (120) and compression springs (130) may be pre-loaded to establish an initial cumulative contraction force at zero circumferential displacement of bodies (102). FIG. 8 depicts an exemplary line graph (150) for such a version of device (100). Curve (152) represents a contraction force exerted by extension springs (120) in response to circumferential displacement of bodies (102). Curve (154) represents a contraction force exerted by compression springs (130) in response to circumferential displacement of bodies (102). Curve (156) represents a cumulative contraction force exerted by springs (120, 130), collectively, in response to circumferential displacement of the bodies (102).

As shown by spring force curves (152, 154) of graph (150), extension springs (120) and compression springs (130) exert progressively increasing contraction forces as circumferential separation of bodies (102) increases during expansion of device (100). Because magnets are omitted from bodies (102) in this version of device (100), the resulting cumulative force as shown by curve (156) continuously increases as device (100) expands. Specifically, the resulting cumulative force continuously increases from a minimum cumulative force at zero circumferential displacement of bodies (102), to a maximum cumulative force at the maximum circumferential displacement (M) of bodies (102).

It will be appreciated that the magnets and/or springs (120, 130) of the two exemplary configurations of device (100) graphically depicted by graphs (140, 150) are suitably configured such that the minimum cumulative contraction force exhibited throughout the operational range of device (100) is high enough to prevent gastric reflux from into esophagus (2). Additionally, the maximum cumulative contraction force exhibited throughout the operational range of device (100) is low enough to be overcome by a food bolus passing through the portion of esophagus (2) encircled by device (100) during peristaltic swallowing; and is also low enough to permit vomiting and venting of gasses from stomach (4) through the encircled portion of esophagus (2). Furthermore, it will be appreciated that the spring rates of extension springs (120) and compression springs (130), as well as the tesla value of the optional magnets, may be selected as desired to achieve any desired profile for cumulative force curves (148, 156) of graphs (140, 150).

B. Sphincter Augmentation Devices Having Spiral Springs

Figure 9A:
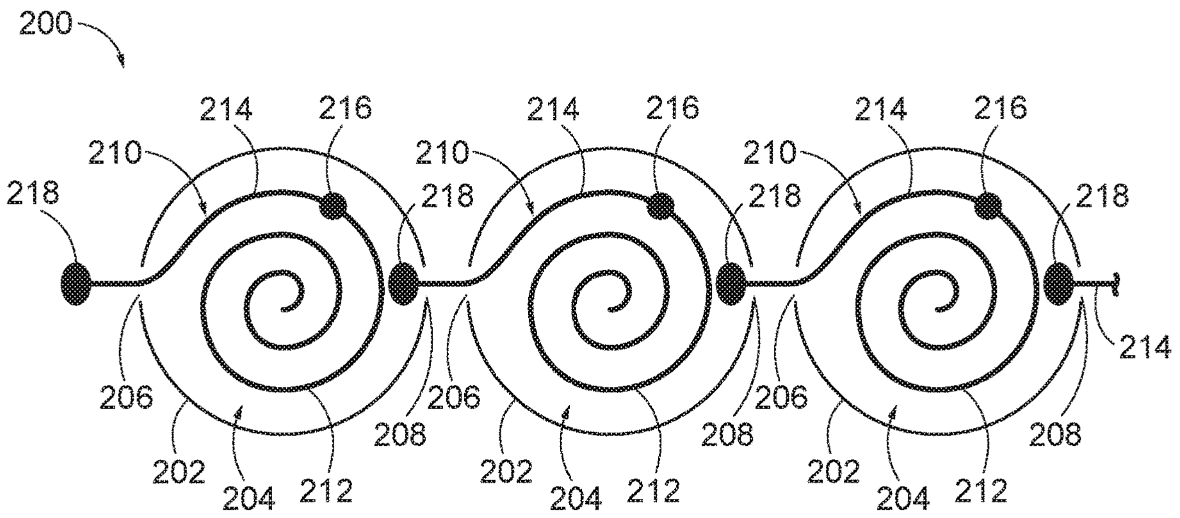
FIG. 9A depicts a schematic cross-sectional top view of a portion of another exemplary sphincter augmentation device having spiral springs, showing the device in a contracted state.
Figure 9B:
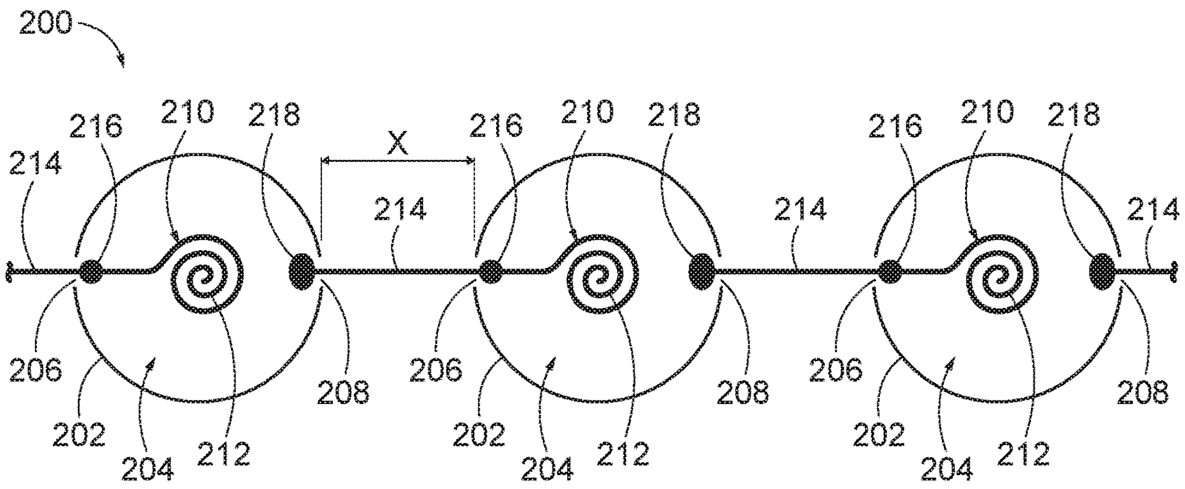
FIG. 9B depicts a schematic cross-sectional top view of the portion of the sphincter augmentation device of FIG. 9A, showing the device in an expanded state.
Figure 11:
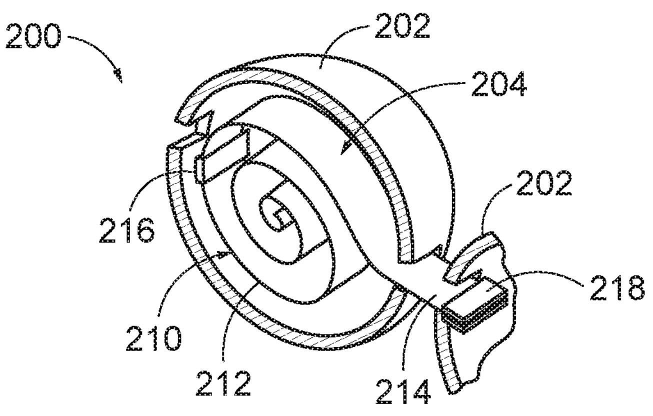
FIG. 11 depicts a cross-sectional isometric view of a portion of the sphincter augmentation device of FIG. 9A.

FIGS. 9A-9B and 11 show a portion of another exemplary sphincter augmentation device (200) having a plurality of bodies (202) that are interlinked by segments integrally coupled with resilient members (210) housed within bodies (202), as described below. Similar to devices (20, 100) described above, device (200) includes a pair of opposed ends (not shown) configured to releasably couple together to secure bodies (202) in a loop formation around an anatomical passageway of a patient, such as esophagus (2). For instance, the opposed ends of device (100) may include coupling features similar to fastener features (50) described above or any of the exemplary coupling features of the references incorporated by reference herein.

Each body (202) of sphincter augmentation device (200) is formed with a generally bead-like shape having a hollow interior (204) and a pair of side openings (206, 208) formed in opposed sides of body (202) that confront adjacent bodies (202). Resilient members (210) are in the form of leaf-type spiral springs, each having a coiled portion (212) defining an inner end of spring (210), and an outer arm (214) extending distally (i.e., away) from coiled portion (212) and defining an outer end of spring (210). Each spiral spring (210) is housed by a respective body (202) such that coiled portion (212) is located within body interior (204) and the inner end of coiled portion (212) is securely anchored to body (202). Outer arm (214) of spiral spring (210) extends outwardly through a first side opening (206) of the body (202) and into a second side opening (208) of an adjacent body (202).

Each spiral spring (210) includes a proximal stop element (216) fixed at a proximal end of outer arm (214), along an outer curvature of spring (210). Each spiral spring (210) further includes a distal stop element (218) fixed at the distal end of outer arm (214). Stop elements (216, 218) are sized larger than body side openings (206, 208) such that proximal stop element (216) is retained within a first body (202) and distal stop element (218) is retained within an adjacent second body (202). Side openings (206, 208) are sized larger than outer arms (214) such that outer arms (214) are slidable through side openings (206, 208). Each outer arm (214) in combination with its respective stop elements (216, 218) defines an expansion limiting member configured to limit resilient deflection of the respective spiral spring (210) and thus expansion of device (100), as described below. Accordingly, the combination of outer arms (214) and stop elements (216, 218) of device (200) collectively define a plurality of discrete expansion limiting members that extend discontinuously along the length of device (200), in contrast to the continuous cable (110) of device (100) described above.

FIG. 9A shows sphincter augmentation device (200) in a contracted state in which spiral springs (210) are at rest. When a radially outwardly directed expansion force is applied to the inner diameter of device (200) (e.g., by a food bolus passing through the encircled portion of esophagus (2)), bodies (202) slidably separate from one another circumferentially along outer arms (214) of spiral springs (210) to enable device (200) to expand radially and circumferentially. Because the distal ends of spiral spring outer arms (214) are captured within the adjacent bodies (202) by distal stop elements (218), each distal stop element (218) serves as a distal anchor point for the respective spiral spring (210). Accordingly, when a first body (202) is forced to circumferentially separate from an adjacent second body (202) upon application of an expansion force, the spiral spring (210) housed within the first body (202) pulls against its anchored distal stop element (218) such that the spiral spring (210) resiliently extends via spiral tightening about its anchored inner end within the first body (202).

Resilient extension of spiral springs (210) enables outer arms (214) to slidably extend outwardly through body side openings (206, 208) until proximal stop elements (216) abut the inner walls of the respective bodies (202), as shown in FIG. 9B, thereby preventing further extension of spiral springs (210). In this fully expanded state of device (200), a full length of each outer arm (214) is exposed externally between adjacent bodies (202). When the expansion force applied to device (200) is released, device (200) automatically returns to its contracted state shown in FIG. 9A. In particular, spiral springs (210) resiliently contract to draw outer arms (214) back into body interiors (204), thereby drawing bodies (202) closer together and into confrontation with one another.

It will be appreciated that each proximal stop element (216) may be spaced proximally from its respective distal stop element (218) along the respective outer arm (214) by any suitable distance (X) (shown in FIG. 9B) to provide device (200) with a desired maximum circumference in the fully expanded state. Additionally, spiral springs (210) of device (200) may be configured with the same spring rate or with differing spring rates. For instance, a first plurality of spiral springs (210) may be configured with a first spring rate while a second plurality of spiral springs (210) may be configured with a second spring rate, such that the combination and arrangement of the first and second spring rates causes device (200) to resiliently expand and contract in a particular desired manner. Such versions of device (200) are configured with a progressive spring rate.

Figure 10:
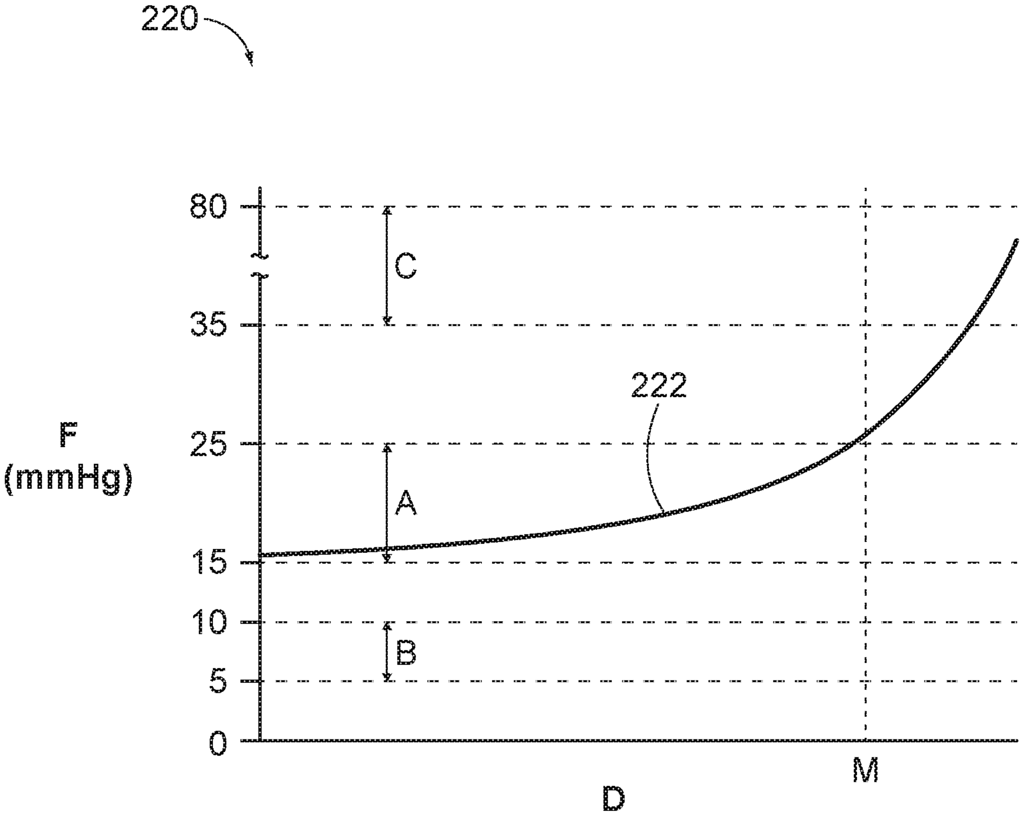
FIG. 10 depicts a line graph illustrating an exemplary relationship between displacement and resulting contraction force exhibited by the spiral springs of the sphincter augmentation device of FIG. 9A.

FIG. 10 shows an exemplary line graph (220) for a version of sphincter augmentation device (200) in which spiral springs (210) all have the same spring rate. Similar to graphs (140, 150) described above, the x-axis of graph (220) indicates circumferential separation (or displacement) (e.g., in millimeters or inches) of a given body (202) relative to an adjacent body (202), starting from the fully contracted state of device (200). The y-axis of graph (220) indicates resulting contraction forces exerted by spiral springs (210) in millimeters of mercury (mmHg), in response to such circumferential displacement. Maximum circumferential displacement between adjacent bodies (202), as defined by spring outer arms (214) in combination with stop elements (216, 218), is indicated on graph (220) by vertical dashed line (M). Accordingly, the portion of graph (220) extending between zero circumferential displacement and maximum circumferential displacement (M) corresponds to an operational range of device (200).

Curve (222) of graph (220) represents a contraction force exerted by spiral springs (210) in response to circumferential displacement of bodies (202). Spiral springs (210) of the illustrated example are pre-tensioned to establish an initial contraction force at zero circumferential displacement of bodies (202). As shown by curve (222), spiral springs (210) exert a progressively increasing contraction force as circumferential separation of bodies (202) increases during expansion of device (200). Specifically, the contraction force increases continuously from a minimum contraction force at zero circumferential displacement of bodies (202) to a maximum contraction force at the maximum circumferential displacement (M) of bodies (202). As shown in graph (220), device (200) of the present example exhibits a contraction force that ranges from approximately 15 mmHg to 25 mmHg, indicated as force range (A) on graph (150).

As also shown in graph, gastric reflux forces generally range from approximately 5 mmHg to 10 mmHg, indicated as force range (B) on graph (220); and peristaltic swallowing forces generally range from approximately 35 mmHg to 80 mmHg, indicated as force range (C) on graph (220). Accordingly, spiral springs (210) are suitably configured such that the contraction forces exerted by device (200) throughout its operational range are high enough to prevent gastric reflux into esophagus (2) yet low enough to permit peristaltic swallowing, as well as vomiting and venting of gasses from stomach (4). It will be appreciated that the biasing members of the other exemplary sphincter augmentation devices (100, 200, 300, 400, 500, 600) described herein may be configured in a similar manner.

Figure 12:
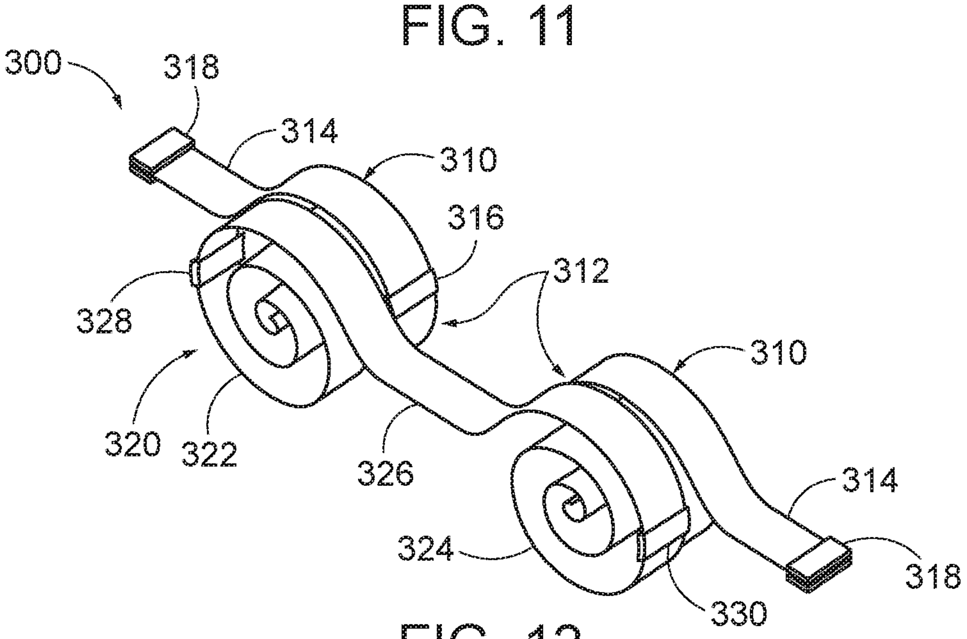
FIG. 12 depicts a cross-sectional isometric view of a portion of another exemplary sphincter augmentation device having spiral springs.

FIG. 12 shows a portion of exemplary alternative sphincter augmentation device (300) that is similar to device (200) described above except as otherwise described below. Device (300) includes a plurality of bodies (not shown), which may be similar to bodies (202), that are interlinked by portions of spiral springs (310, 320) housed within the bodies. Device (300) includes a plurality of single spiral springs (310) and a plurality of double spiral springs (320), with only one double spiral spring (320) being shown in the present illustration. Each single spiral spring (310) is similar in structure and function to spiral springs (210) described above in that single spiral spring (310) includes a single coiled portion (312), an outer arm (314) extending away from coiled portion (312), a proximal stop element (316) fixed at a proximal end of outer arm (314), and a distal stop element (318) fixed at a distal end of outer arm (314).

Each double spiral spring (320) of sphincter augmentation device (300) includes a first coiled portion (322) wound in a first direction, and a second coiled portion (324) spaced apart from first coiled portion (322) and wound in an opposite second direction. Double spiral spring (320) further includes a link (326) that extends between the outer ends of first and second coiled portions (322, 324) and which is formed integrally therewith. Accordingly, link (326) defines an outer arm corresponding to each coiled portion (322, 324). Each double spiral spring (320) further includes a first stop element (328) fixed at a first end of link (326) that joins integrally with first coiled portion (322), and a second stop element (330) fixed at a second end of link (326) that joins integrally with second coiled portion (324). Stop elements (316, 318, 328, 330) of single spiral springs (310) and double spiral springs (320) are configured to function in a manner similar to stop elements (216, 218) of spiral springs (210) described above.

Spiral springs (310, 320) are arranged within the bodies of sphincter augmentation device (300) such that each body houses the coiled portion (312) of a single spiral spring (310)

and a coiled portion (322, 324) of a double spiral spring (320). In particular, a single spiral spring (310) is oriented within the body so that its outer arm (314) extends outwardly through a first side opening of the body, and a coiled portion (322, 324) of a double spiral spring (320) is oriented within the body so that link (326) extends outwardly through an opposed second side opening of the body. In the present version, coiled portions (322, 324) of double spiral springs (320) are positioned toward an inner diameter side of the bodies, and coiled portions (312) of single spiral springs (310) are positioned toward an outer diameter side of the bodies. Additionally, inner ends of coiled portions (312, 322, 324) are anchored coaxially within each body. Accordingly, single and double spiral springs (310, 320) are arranged about the circumference of device (300) such that outer arms (314) and links (326) alternate as the expansion limiting member that extends between, and thereby links, adjacent pairs of the bodies.

Each of single spiral springs (310) and double spiral springs (320) resiliently extends and retracts in a manner similar to spiral springs (210) described above. In particular, when a radially outwardly directed expansion force is applied to the inner diameter of device (300) (e.g., by a food bolus passing through the encircled portion of esophagus (2)), the bodies of device (300) slidably separate from one another circumferentially along outer arms (314) of single spiral springs (310) and links (326) of double spiral springs (320). In doing so, the coiled portion (312) of each single spiral spring (310) pulls against its anchored distal stop element (318) such that single spiral springs (310) resiliently extend. Additionally, coiled portions (322, 324) of each double spiral spring (320) pull against one another in opposing directions, via link (326), such that both coiled portions (322, 324) resiliently extend. In some versions, single spiral springs (310) may be configured with a first spring rate while double spiral springs (320) are configured with a different second spring rate. In such versions, single spiral springs (310) are configured to begin extending before or after double spiral springs (320) begin extending when an expansion force is applied to device (300). Accordingly, in such versions, device (300) is configured with a progressive spring rate, similar to some versions of devices (100) described above. In other versions, single spiral springs (310) may be configured with the same spring rate as double spiral springs (320), such that single and double spiral springs (320) all extend simultaneously in response to an applied expansion force.

Similar to sphincter augmentation device (200) described above, expansion of device (300) is restricted by stop elements (316, 318, 328, 330). In particular, proximal stop elements (316) of single spiral springs (310) and stop elements (328, 330) of double spiral springs (320) are configured to abut the inner walls of their respective device bodies in unison and thereby limit expansion of device (300). It will be appreciated that stop elements (316, 328, 330) may be fixed at any suitable location along their respective spiral spring (310, 320) to provide for a desired maximum circumference of device (300) in the fully expanded state.

Figure 13:
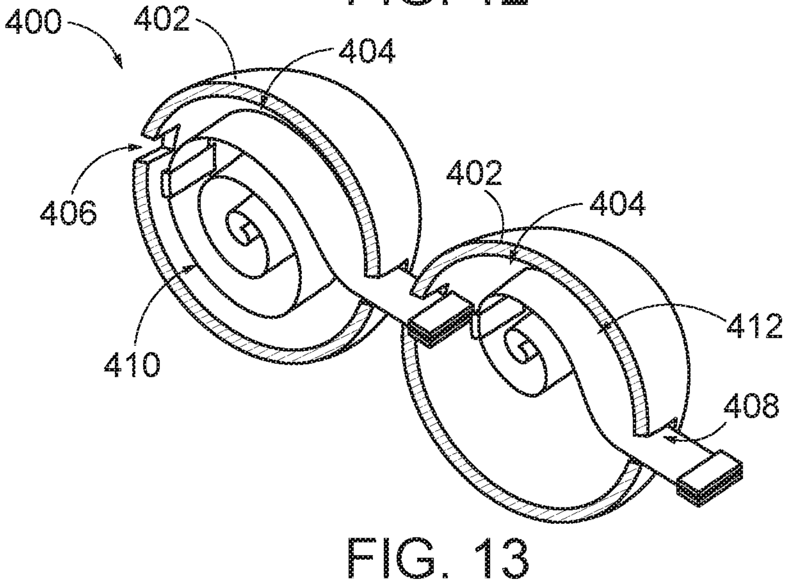
FIG. 13 depicts a cross-sectional isometric view of a portion of another sphincter augmentation device having spiral springs.

FIG. 13 shows a portion of yet another exemplary sphincter augmentation device (400) that incorporates spiral springs (410, 412). Device (400) is similar to devices (200, 300) described above in that device (400) has a plurality of interlinked bodies (402) each having a hollow interior (404) and a pair of side openings (406, 408) arranged in opposed sides of each body (402). Device (400) further includes a plurality of first spiral springs (410) each configured with a first spring rate, and a plurality of second spiral springs (412) each configured with a second spring rate less than the first spring rate. Each spiral spring (410, 412) is otherwise individually configured and operable in a manner similar to spiral springs (210, 310) of devices (200, 300) described above. Because each first spiral spring (410) has a greater spring rate than each second spiral spring (412), second spiral springs (412) are configured to resiliently extend before first spiral springs (410) in response to an expansion force applied to device (400). Accordingly, similar to versions of devices (100, 300) described above, device (400) is configured with a progressive spring rate.

Though not shown, it will be appreciated that any of the exemplary sphincter augmentation devices (200, 300, 400) described above may further include a plurality of permanent magnets housed within their respective bodies. Such magnets may be configured to magnetically attract one another and thus cooperate with spiral springs (210, 310, 320, 410, 412) to bias devices (200, 300, 400) toward the contracted state, similar to magnets (60) of device (20) described above.

Figure 14A:
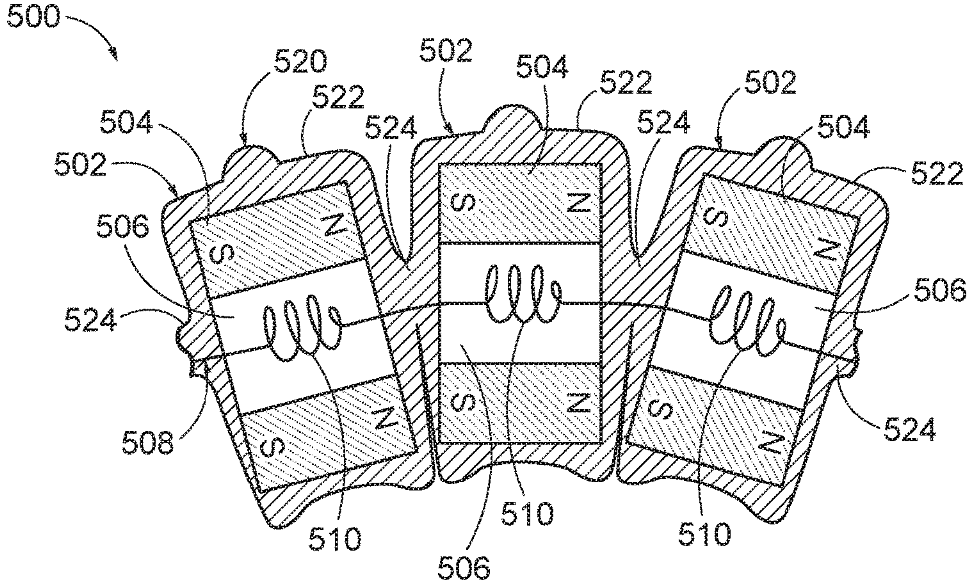
FIG. 14A depicts a cross-sectional top view of a portion of another exemplary sphincter augmentation device having an elastically deformable outer jacket, showing the device in a contracted state.
Figure 14B:
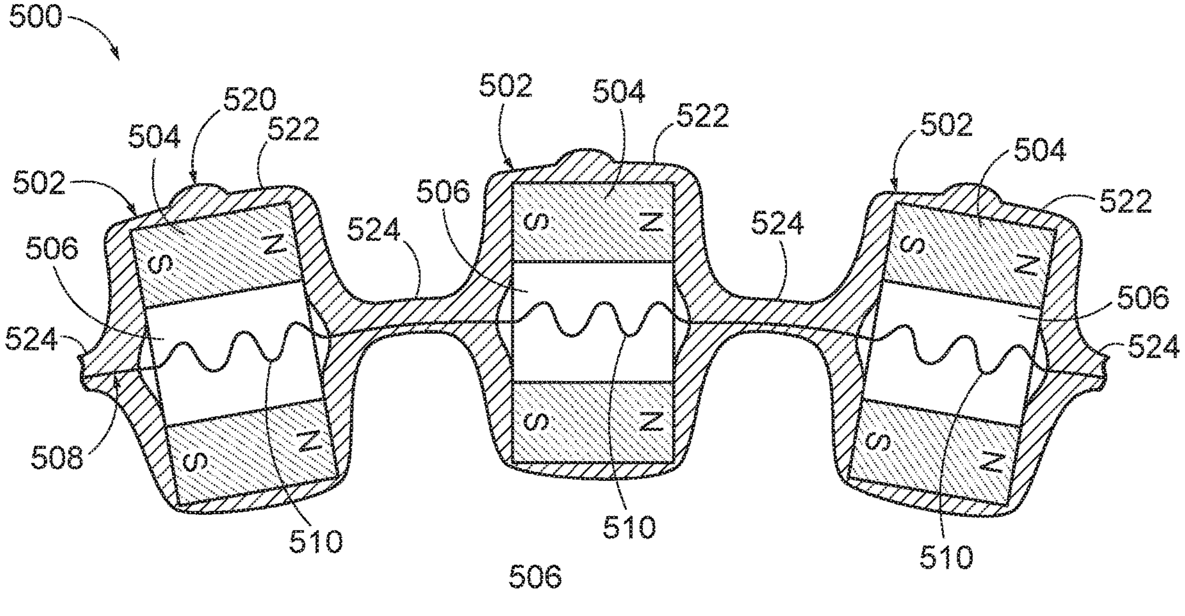
FIG. 14B depicts a cross-sectional top view of the portion of the sphincter augmentation device of FIG. 14A, showing the device in an expanded state.

C. Sphincter Augmentation Device Having Magnets Encapsulated by Elastomeric Outer Jacket In some instances, it may be desirable to use resilient features other than traditional springs to interlink the bodies of a sphincter augmentation device. FIGS. 14A-14B show another exemplary sphincter augmentation device (500) having such a configuration. Similar to devices (100, 200, 300, 400) described above, device (500) is configured to be positioned and implanted about an anatomical passageway of a patient, such as esophagus (2).

Sphincter augmentation device (500) includes a plurality of interlinked bodies (502) each having an annular rare-earth permanent magnet (504) defining a central chamber (506) through which an elongate expansion limiting member (508) extends, as described in greater detail below. Similar to devices (100, 200, 300, 400), device (500) includes a pair of opposed ends (512, 514) (see FIG. 15B) configured to releasably couple together to secure bodies (502) in a loop formation about an anatomical passageway of a patient. Magnets (504) are configured to magnetically attract one another to bias device (500) toward a radially contracted state about the anatomical passageway, similar to magnets (60) of device (20) described above.

Device (500) further includes an elastomeric outer jacket (520) that encapsulates magnets (504) to define bodies (502). Outer jacket (520) is formed as a unitary support structure having a plurality of capsules (522) that encapsulate magnets (504), and a corresponding plurality of webs (524) that interlink and are formed integrally with capsules (522). As shown in FIGS. 14A and 14B, outer jacket (520) is configured to resiliently deform and thereby permit device (500) to transition between a radially contracted state (FIG. 14A) and a radially expanded state (FIG. 14B). Outer jacket (520) cooperates with magnets (504) to bias device (500) toward the radially contracted state. As shown in FIG. 14A, bodies (502) are configured to abut and compress against one another when device (500) is in the radially contracted state such that capsules (522) and webs (524) swell radially. As device (500) expands radially, capsules (522) and webs (524) resiliently expand circumferentially and simultaneously contract radially, as shown in FIG. 14B.

Expansion limiting member (508) of sphincter augmentation device (500) is shown in the form of an elongate cable that is anchored at first and second device ends (512, 514). Cable (508) extends continuously and slidably through webs (524) and the corresponding sidewalls of capsules (522).

Cable (508) includes a plurality of resilient portions (510) spaced longitudinally along the length of cable (508). Each resilient portion (510) is shaped similar to an extension spring and is located within a respective chamber (506) of a device body (502). As shown in FIGS. 14A and 14B, resilient portions (510) are configured to resiliently extend as device (500) expands radially, thereby enabling device (500) to assume a larger circumference. Upon reaching a fully extended state, cable (508) restricts further radial and circumferential expansion of device (500). As device (500) returns to the radially contracted state shown in FIG. 14A, resilient portions (510) also return to their contracted states. Accordingly, resilient portions (510) of cable (508) may cooperate with webs (524) and capsules (522) of outer jacket (520), and with magnets (504) housed therein, to bias device (500) toward the radially contracted state.

While cable (508) is shown having a plurality of resilient portions (510) in the present example, it will be appreciated that cable (508) may be configured in various alternative manners suitable to enable cable (508) to resiliently extend and contract lengthwise in other examples. For instance, and by way of example only, resilient portions (510) may be omitted and cable (508) may be formed of an elastic material such that an entirety of cable (508) is configured to resiliently extend and contract as device (500) transitions between the radially contracted state and the radially expanded state.

Figure 15A:
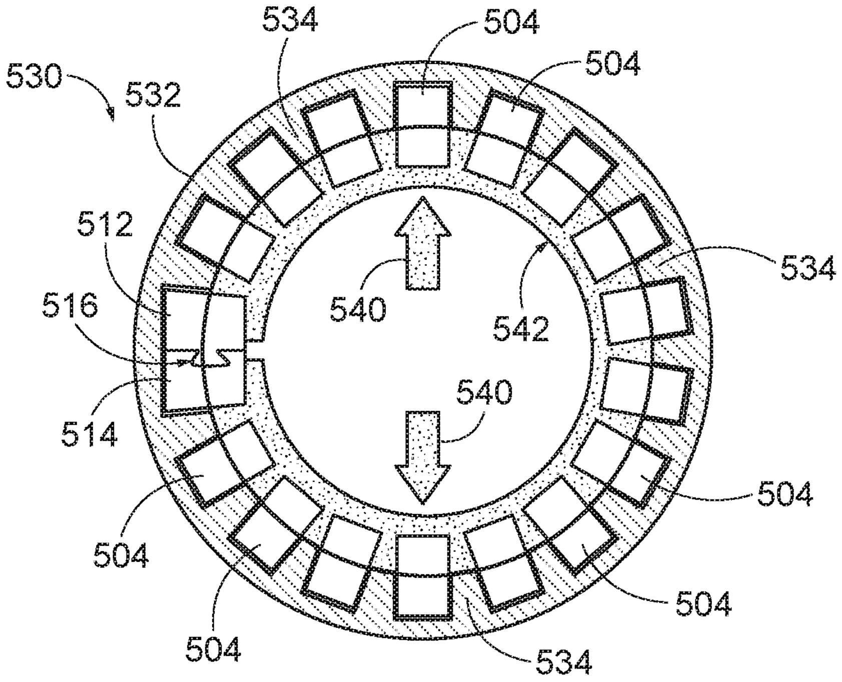
FIG. 15A depicts a schematic top plan view of an exemplary arrangement for performing a first step in forming the sphincter augmentation device of FIG. 14A.
Figure 15B:
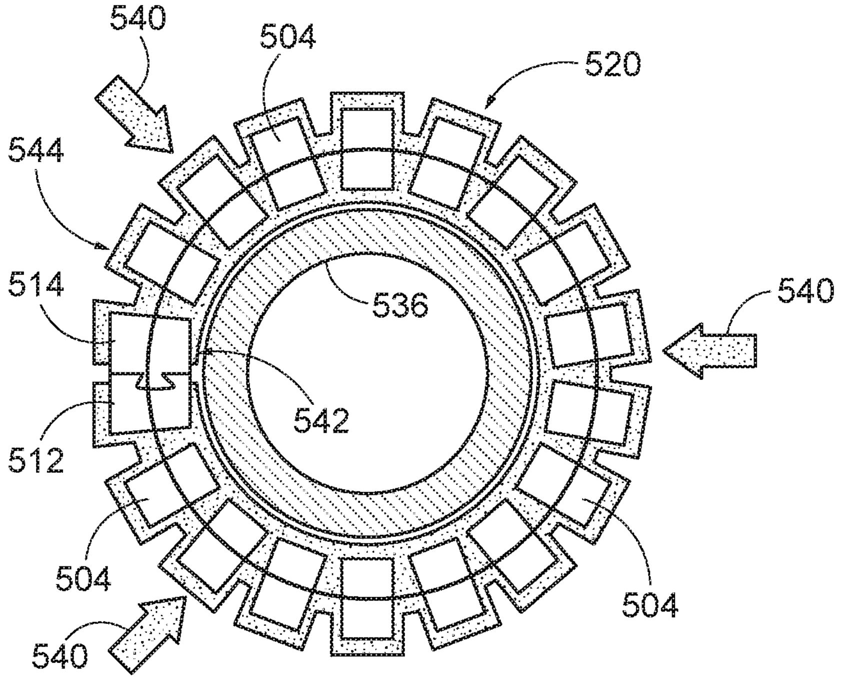
FIG. 15B depicts a schematic top plan view of an exemplary arrangement for performing a second step in forming the sphincter augmentation device of FIG. 14A.

FIGS. 15A-15B show an exemplary jig assembly (530) and corresponding steps for forming elastomeric outer jacket (520) about magnets (504) and cable (508) to define sphincter augmentation device (500) described above. Jig assembly (530) comprises an annular outer jig member (532) and an annular inner jig member (536). In some versions, jig members (532, 536) may be components of a mold structure configured to facilitate formation of outer jacket (520) via injection molding. As shown in FIG. 15A, magnets (504) are arranged circumferentially about an inner diameter of outer jig member (532), and cable (508) is directed through chambers (506) of magnets (504) and secured to device ends (512, 514), which are coupled together via a clasp feature (516). The inner diameter of outer jig member (532) includes a plurality of inwardly extending projections (534) between which magnets (504) and device ends (512, 514) are positioned to thereby stabilize magnets (504) and ends (512, 514) in a loop formation. Molten elastomer material (540) is then injected along the inner diameter side of magnets (504) and device ends (512, 514) in a radially outward direction, thereby forming a radially inner portion (542) of jacket (520). As shown in FIG. 15B, outer jig member (532) is then removed and inner jig member (536) is inserted along the inner diameter of the newly formed radially inner portion (542) of jacket (520). Molten elastomer material (540) is then injected along the outer diameter side of magnets (504) and device ends (512, 514), thereby forming a radially outer portion (544) of jacket (520) that joins integrally with radially inner portion (542).

It will be appreciated that the steps shown in FIGS. 15A and 15B are merely one example of a process for forming elastomeric outer jacket (520) about magnets (504) to define sphincter augmentation device (500). Various other suitable methods will be readily apparent to those of ordinary skill in the art. Moreover, it will be appreciated that an elastomeric outer jacket similar to jacket (520) may be applied to any of the other exemplary sphincter augmentation devices (100, 200, 300, 400) described above.

Figure 16A:
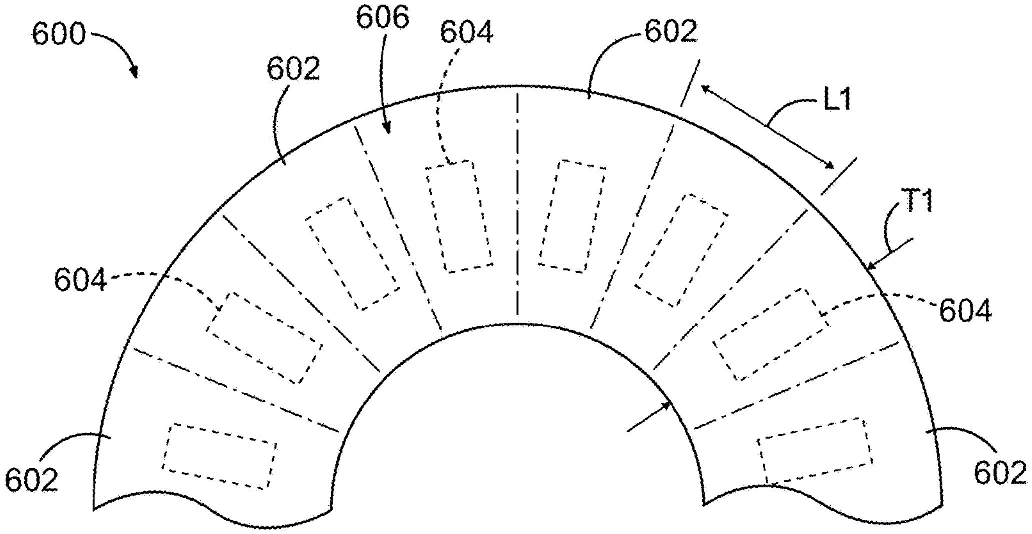
FIG. 16A depicts a schematic top plan view of a portion of another exemplary sphincter augmentation device having an elastically deformable outer jacket, showing the device in a contracted state.
Figure 16B:
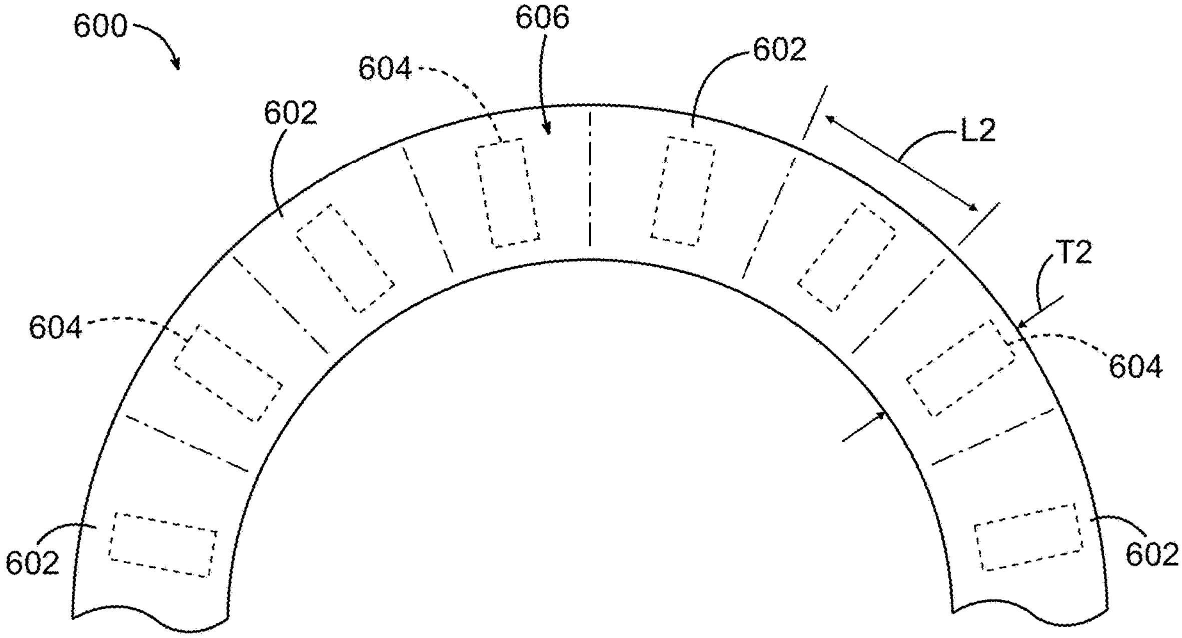
FIG. 16B depicts a schematic top plan view of the portion of the sphincter augmentation device of FIG. 16A, showing the device in an expanded state.

FIGS. 16A-16B shows a portion of an exemplary alternative sphincter augmentation device (600) that is similar to device (500) described above, except as otherwise described below. Like device (500), device (600) includes a plurality of interlinked bodies (602) each having a rare-earth permanent magnet (604) housed therein. Magnets (604) may be annular like magnets (504) described above, each defining an inner chamber (not shown). Device (600) may further include an expansion limiting feature (not shown), similar to cable (508) described above, configured to limit expansion of device (600). Device (600) further includes a unitary, elastomeric outer jacket (606) that encapsulates magnets (504) and is configured to enable device (500) to resiliently expand radially and circumferentially from a contracted state, shown in FIG. 16A, to an expanded state, shown in FIG. 16B. Similar to jacket (520), jacket (606) cooperates with magnets (604) to bias device (600) toward the contracted state.

In contrast to elastomeric outer jacket (520) described above, jacket (606) omits webs (524) such that the outer surface of jacket (520) defines a uniform, ring-like shape about the circumference of device (600). As device (600) expands radially and circumferentially in response to an applied expansion force, bodies (602) elastically lengthen in a circumferential direction and simultaneously contract in a radial direction. Accordingly, bodies (602) transition from the disk shapes seen in FIG. 16A to the elongate cylinder shapes seen in FIG. 16B. In particular, a circumferential length of bodies (602) elastically expands from a first circumferential length (L1) to a second circumferential length (L2); and simultaneously, a radial thickness of bodies (602) decreases from a first radial thickness (T1) to a second radial thickness (T2). Accordingly, device (500) is configured to resiliently expand via resilient expansion of each body (602), rather than separation of bodies (602) as shown in connection with devices (100, 200, 300, 400) described above, which are interlinked by springs.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A sphincter augmentation device, comprising: (a) a plurality of interlinked bodies; (b) a pair of device ends configured to releasably couple together to secure the bodies in a loop formation sized to fit around an internal anatomical passageway of a patient; (c) a plurality of resilient members, wherein each resilient member extends between an adjacent pair of the bodies, wherein the resilient members are configured to elastically deform to permit the device to transition between a radially contracted state and a radially expanded state, wherein the resilient members are configured to bias the device toward the radially contracted state in which the device is configured to exert an inwardly directed force on the anatomical passageway to selectively limit passage of fluids therethrough; and (d) an expansion limiting member extending between an adjacent pair of the bodies, wherein the expansion limiting member is slidably received by at least one of the bodies, wherein the expansion limiting member is configured to limit radial expansion of the device.

Example 2

The sphincter augmentation device of Example 1, wherein each of the resilient members includes a first member end and a second member end, wherein the first member end is retained by a first body of the bodies, wherein the second member end is retained externally of the first body.

Example 3

The sphincter augmentation device of Example 2, wherein the first member end is housed within the first body, wherein the second member end is housed within an adjacent second body.

Example 4

The sphincter augmentation device of any of the preceding Examples, wherein the plurality of resilient members exhibits a first spring rate and a second spring rate, wherein the first and second spring rates are different.

Example 5

The sphincter augmentation device of Example 4, wherein the plurality of resilient members comprises a plurality of first resilient members that exhibit the first spring rate, and a plurality of second resilient members that exhibit the second spring rate.

Example 6

The sphincter augmentation device of any of the preceding Examples, wherein the plurality of resilient members comprises a plurality of extension springs.

Example 7

The sphincter augmentation device of Example 6, wherein each extension spring comprises a first end retained within a body of the bodies, and an opposed second that extends externally of the body, wherein the first end is coupled with a compression spring housed within the body.

Example 8

The sphincter augmentation device of any of the preceding Examples, wherein the plurality of resilient members comprises a plurality of a spiral springs, wherein each spiral spring is at least partially housed within a respective body of the bodies.

Example 9

The sphincter augmentation device of any of the preceding Examples, further comprising a plurality of magnets housed within the bodies, wherein the magnets are configured to magnetically attract one another to bias the device toward the radially contracted state.

Example 10

The sphincter augmentation device of Example 9, further comprising an elastomeric jacket that encapsulates the magnets, wherein the elastomeric jacket defines the resilient members, wherein the elastomeric jacket is configured to elastically deform to enable the device to transition between the radially contracted state and the radially expanded state.

Example 11

The sphincter augmentation device of any of the preceding Examples, wherein the expansion limiting member comprises an elongate member that extends continuously between the device ends and through the bodies.

Example 12

The sphincter augmentation device of Example 11, wherein the elongate member includes a resilient portion, wherein the resilient portion is configured to elastically deform when the device transitions from the radially contracted state to the radially expanded state.

Example 13

The sphincter augmentation device of any of the preceding Examples, further comprising a plurality of expansion limiting members arranged discontinuously between the device ends, where each of the expansion limiting members extends between an adjacent pair of the bodies.

Example 14

The sphincter augmentation device of Example 13, wherein the expansion limiting members are integral with the resilient members.

Example 15

The sphincter augmentation device of any of Examples 13 through 14, wherein each expansion limiting member comprises first and second stop elements coupled with a respective one of the resilient members, wherein when the device reaches the radially expanded state the first stop element is configured to arrest a first portion of the resilient member relative to a first body of the bodies and the second stop element is configured to arrest a second portion of the resilient member relative to an adjacent second body of the bodies.

Example 16

A sphincter augmentation device, comprising: (a) a plurality of interlinked bodies; (b) a pair of ends configured to releasably couple together to secure the bodies in a loop formation sized to fit around an internal anatomical passageway of a patient; (c) a plurality of first resilient members coupled with the bodies, wherein each of the first resilient members exhibits a first spring rate; (d) a plurality of second resilient members coupled with the bodies, wherein each of the second resilient members exhibits a second spring rate different than the first spring rate, wherein the first and second resilient members are configured to elastically deform to permit the device to transition between a radially contracted state and a radially expanded state, wherein the first and second resilient members are configured to cooperate to bias the device toward the radially contracted state in which the device is configured to exert an inwardly directed force on the anatomical passageway to selectively limit passage of fluids therethrough.

Example 17

The sphincter augmentation device of Example 16, wherein the first resilient members comprise at least one of extension springs or spiral springs.

Example 18

The sphincter augmentation device of any of Examples 16 through 17, further comprising an elastomeric outer jacket that defines the first resilient members, wherein the second resilient members are housed within the bodies.

Example 19

A sphincter augmentation device, comprising: (a) a plurality of magnets; (b) an outer jacket that encapsulates the magnets to define a plurality of interlinked bodies; and (c) a pair of ends configured to releasably couple together to secure the bodies in a loop formation sized to fit around an internal anatomical passageway of a patient; wherein the outer jacket is configured to elastically deform to permit the device to transition between a radially contracted state and a radially expanded state, wherein the outer jacket and the magnets are configured to cooperate to bias the device toward the radially contracted state in which the device is configured to exert an inwardly directed force on the anatomical passageway to selectively limit passage of fluids therethrough.

Example 20

The sphincter augmentation device of Example 19, wherein the outer jacket comprises an elastomer.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A sphincter augmentation device, comprising:

(a) a plurality of magnets;

(b) a jacket that encapsulates the magnets to define a plurality of interlinked bodies comprising a first interlinked body and a second interlinked body, wherein the first interlinked body encapsulates a first magnet of the plurality of magnets and the second interlinked body encapsulates a second magnet of the plurality of magnets, wherein each magnet of the plurality of magnets defines a chamber;

(c) a pair of ends configured to releasably couple together to secure the bodies in a loop formation sized to fit around an internal anatomical passageway of a patient; and (d) an expansion limiter extending through each chamber of the plurality of magnets, wherein the jacket is configured to elastically deform to permit the device to transition between a radially contracted state and a radially expanded state, and the expansion limiter is configured to limit expansion of the jacket in the radially expanded state, wherein a first portion of the jacket associated with the first interlinked body and a second portion of the jacket associated with the second interlinked body are configured to contact each other between the first magnet and the second magnet in the radially contracted state, and wherein the device is configured to exert an inwardly directed force on the anatomical passageway to selectively limit passage of fluids therethrough while in the radially contracted state.

2. The sphincter augmentation device of claim 1, wherein the jacket comprises an elastomer.

3. The sphincter augmentation device of claim 1, wherein the jacket comprises a support structure.

4. The sphincter augmentation device of claim 3, wherein the support structure comprises a plurality of webs integrally formed with the jacket.

5. The sphincter augmentation device of claim 3, wherein the support structure comprises a plurality of capsules, wherein each capsule of the plurality of capsules encapsulates a respective magnet of the plurality of magnets.

6. The sphincter augmentation device of claim 5, wherein the support structure further comprises a plurality of webs that interlink the plurality of capsules.

7. The sphincter augmentation device of claim 6, wherein the plurality of capsules and the plurality of webs are configured to swell radially in the radially contracted state.

8. The sphincter augmentation device of claim 1, wherein the expansion limiter comprises a cable.

9. The sphincter augmentation device of claim 8, wherein the cable comprises a plurality of resilient portions spaced along the length of the cable.

10. The sphincter augmentation device of claim 9, wherein the plurality of resilient portions each define a coil shape.

11. The sphincter augmentation device of claim 9, wherein each resilient portion of the plurality of resilient portions is configured to be housed within a respective chamber of the plurality of magnets in the radially contracted state.

12. The sphincter augmentation device of claim 9, wherein the plurality of resilient portions are configured to cooperate with the jacket to bias the device toward the radially contracted state.

13. The sphincter augmentation device of claim 12, wherein the plurality of resilient portions each comprise an elastic material.

14. A sphincter augmentation device, comprising:

(a) a plurality of magnets;

(b) a jacket that encapsulates the magnets to define a plurality of interlinked bodies, wherein the plurality of interlinked bodies comprises a first interlinked body encapsulating a first magnet of the plurality of magnets and a second interlinked body that is adjacent to the first interlinked body, wherein the second interlinked body encapsulates a second magnet of the plurality of magnets, wherein each magnet of the plurality of magnets defines a chamber;

(c) a pair of ends configured to releasably couple together to secure the bodies in a loop formation sized to fit around an internal anatomical passageway of a patient; and (d) an expansion limiter extending through each chamber of the plurality of magnets, wherein the plurality of interlinked bodies is configured to permit the device to transition between a radially contracted state and a radially expanded state, and the expansion limiter is configured to limit expansion of the jacket in the radially expanded state, wherein the device in the radially contracted state is configured to exert an inwardly directed force on the anatomical passageway to selectively limit passage of fluids therethrough, and wherein a first portion of the jacket associated with the first interlinked body and a second portion of the jacket associated with the second interlinked body are configured to contact each other between the first magnet and the second magnet in the radially contracted state.

15. The sphincter augmentation device of claim 14, wherein the pair of ends comprise a clasping feature.

16. The sphincter augmentation device of claim 14, wherein the jacket comprises an elastomeric jacket.

17. The sphincter augmentation device of claim 16, wherein the elastomeric jacket connects the pair of ends together.

18. A sphincter augmentation device, comprising:

(a) a plurality of magnets;

(b) a jacket that encapsulates the magnets to define a plurality of interlinked bodies, wherein a first magnet of the plurality of magnets is encapsulated in a first interlinked body of the plurality of interlinked bodies and a second magnet of the plurality of magnets is encapsulated in a second interlinked body of the plurality of interlinked bodies, wherein each magnet of the plurality of magnets defines a chamber;

(c) a pair of ends configured to releasably couple together to secure the bodies in a loop formation sized to fit around an internal anatomical passageway of a patient; and (d) an expansion limiter extending through each chamber of the plurality of magnets, wherein the plurality of interlinked bodies is configured to permit the device to transition between a radially contracted state and a radially expanded state, and the first interlinked body is adjacent the second interlocked interlinked body in the radially contracted state, and the expansion limiter is configured to limit expansion of the jacket in the radially expanded state, wherein the device in the radially contracted state is configured to exert an inwardly directed force on the anatomical passageway to selectively limit passage of fluids therethrough, and wherein a first portion of the jacket associated with the first interlinked body and a second portion of the jacket associated with the second interlinked body are configured to contact each other between the first magnet and the second magnet in the radially contracted state.

* * * * *